(12) United States Patent
Wang

(10) Patent No.: US 11,529,285 B2
(45) Date of Patent: Dec. 20, 2022

(54) BODY PHYSIOTHERAPY MACHINE

(71) Applicant: Airbender Co., Inc., Taipei (TW)

(72) Inventor: Chien-Chi Wang, Taipei (TW)

(73) Assignee: Airbender Co., Inc., Taipei (TW)

( * ) Notice: Subject to any disclaimer, the term of this patent is extended or adjusted under 35 U.S.C. 154(b) by 486 days.

(21) Appl. No.: 16/701,256

(22) Filed: Dec. 3, 2019

(65) Prior Publication Data

US 2021/0161760 A1 Jun. 3, 2021

(51) Int. Cl.
| A61H 39/00 | (2006.01) |
| A61H 39/02 | (2006.01) |
| A61B 5/0532 | (2021.01) |
| A61N 1/32 | (2006.01) |
| A61N 1/36 | (2006.01) |
| A61N 1/04 | (2006.01) |

(52) U.S. Cl.
CPC ......... *A61H 39/002* (2013.01); *A61B 5/0532* (2013.01); *A61H 39/007* (2013.01); *A61H 39/02* (2013.01); *A61N 1/0484* (2013.01); *A61N 1/322* (2013.01); *A61N 1/36031* (2017.08); *A61N 1/36034* (2017.08); *A61H 2201/5043* (2013.01); *A61H 2201/5071* (2013.01); *A61H 2201/5082* (2013.01); *A61H 2205/125* (2013.01)

(58) Field of Classification Search
CPC .............. A61H 39/002; A61N 1/36031; A61N 1/36034
USPC .......................................................... 600/548
See application file for complete search history.

(56) References Cited

U.S. PATENT DOCUMENTS

2015/0351690 A1* 12/2015 Toth ........................ A61B 5/282
600/391

FOREIGN PATENT DOCUMENTS

| TW | M546814 U | 11/2017 |
| TW | I619524 B | 1/2018 |
| TW | M570161 | 11/2018 |

* cited by examiner

*Primary Examiner* — Nadia A Mahmood
(74) *Attorney, Agent, or Firm* — Alan D. Kamrath; Karin L. Williams; Mayer & Williams PC

(57) ABSTRACT

A body physiotherapy machine contains a conductive sphere member and a body configured to output electric physiotherapy energy to the conductive sphere member. The conductive sphere member is held by a user to contact his/her discomfort or acupuncture points so as to comfort the user and to enhance metabolism by ways of the electric physiotherapy energy, thus maintaining health easily.

12 Claims, 4 Drawing Sheets

BODY PHYSIOTHERAPY MACHINE

FIELD OF THE INVENTION

The present invention relates to a body physiotherapy machine which is capable of comforting the user and enhancing metabolism.

BACKGROUND OF THE INVENTION

Sub-health has seven symptoms: 1. Tiredness and mental disability. 2. Poor sleep quality. 3. Headache, dizziness. 4. Digestive discomfort. 5. Chest tightness and poor breathing 6. Allergies. 7. Muscle soreness. These sub-health conditions have not yet reached the stage of disease, so it is difficult to check in the Western medicine system. However, the medical theory of prevention of diseases such as "micro-prevention of disease" and "disinfection" is appropriate for sub-health.

The present invention has arisen to mitigate and/or obviate the afore-described disadvantages.

SUMMARY OF THE INVENTION

The primary aspect of the present invention is to provide a body physiotherapy machine which is capable of comforting the user and enhancing metabolism To obtain above-mentioned aspects, a body physiotherapy machine provided by the present invention contains: a body including a power input end configured to electrically connected with a power supply unit, a power processing unit electrically connected with the power input end so as to adjust electric currents from the power supply unit to produce electric physiotherapy energy, a processor connected with the power processing unit, an operation unit electrically connected with the processor, a display unit connected with the processor so as to display physiotherapy energy information, and a first output ends configured to output the electric physiotherapy energy; and a conductive sphere member electrically connected with the first output end and configured to be held by a user so as to contact with the user directly or indirectly, thus sending the electric physiotherapy energy to the user.

DETAILED DESCRIPTION OF THE PREFERRED EMBODIMENTS

A body physiotherapy machine according to a preferred embodiment of the present invention comprises: a body 1.

Figure 1:
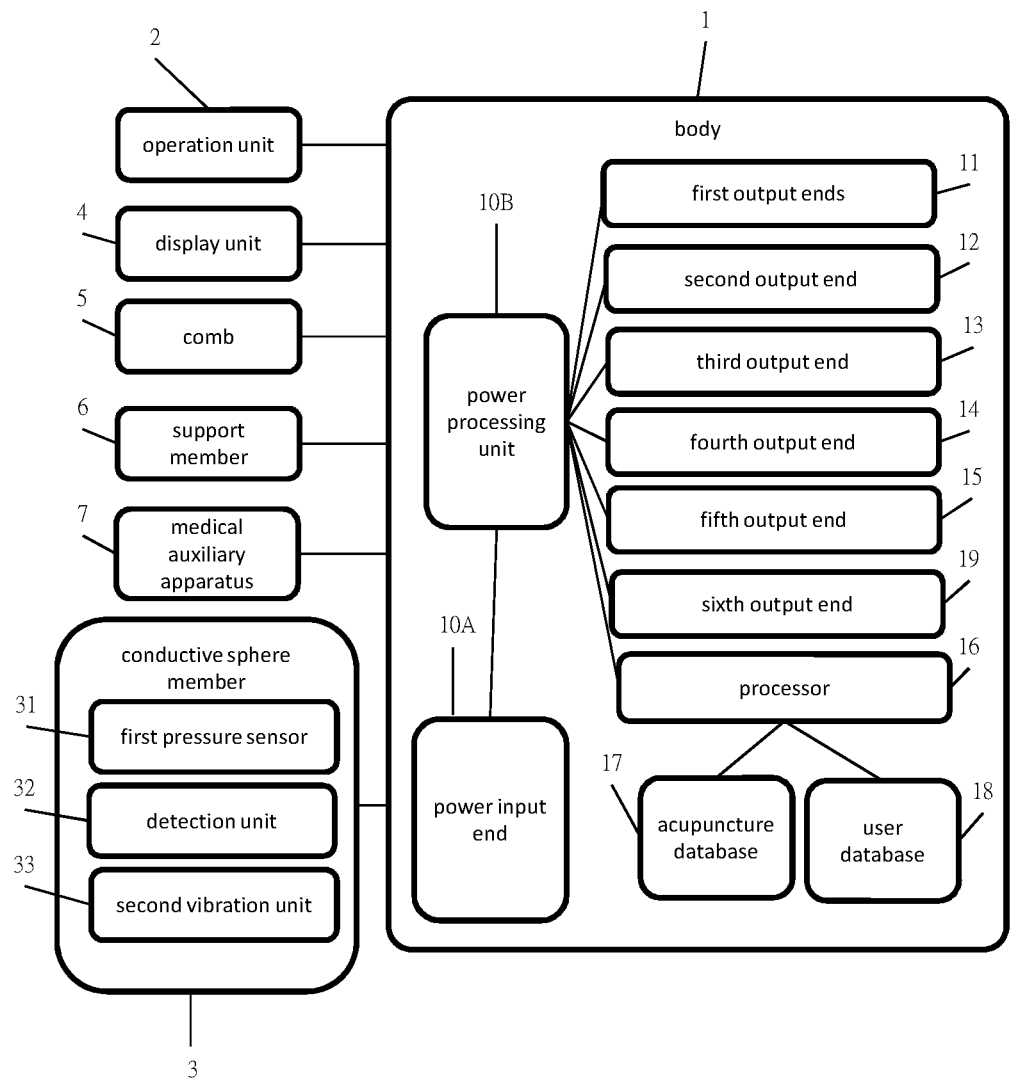
FIG. 1 is a schematic view showing body a physiotherapy machine according to a preferred embodiment of the present invention.

With reference to FIG. 1, the body 1 includes a power input end 10A configured to electrically connected with a power supply unit, a power processing unit 10B electrically connected with the power input end 10A so as to adjust electric currents from the power supply unit to produce electric physiotherapy energy, a processor 16 connected with the power processing unit 10B, an operation unit 2 electrically connected with the processor 16, a display unit 4 connected with the processor 16 so as to display physiotherapy energy information, and a first output end 11, a second output end 12, a third output end 13, a fourth output end 14 and a fifth output end 15 which are configured to output the electric physiotherapy energy. Preferably, the power processing unit 10B is configured to adjust the electric currents and voltage and to change a current frequency and electrical waveform from the power supply unit, thus producing the electric physiotherapy energy. The operation unit 2 is mounted outside the body 1 and is connected with the processor 16 via a signal wire or in a wireless manner. The operation unit 2 is configured to set power parameters of the electric physiotherapy energy, wherein the power parameters includes a current value, a voltage value, the current frequency, and an operating time so that user adjusts the electric physiotherapy energy based on his/her health status freely. The operation unit 2 is set in a fixed time, wherein the current frequency of the power parameters is more than $10^6$ Hz so as to provide the electric physiotherapy energy to a user's body and to vibrate the user's body physically. The processor 16 controls the operation unit 10B based on an operating status of the operation unit 2.

Referring to FIG. 1, the body 1 further includes a conductive sphere member 3 electrically connected with the first output end 11 and configured to be held by the user so as to contact with the user directly or indirectly, thus sending the electric physiotherapy energy to the user.

Accordingly, the body physiotherapy machine facilitates the user's health, for example, the conductive sphere member 3 contacts with the user or acupuncture points of the user so that the electric physiotherapy energy is sent to the user to activate cells and to enhance metabolism and immunity.

Preferably, a pressure forced onto the conductive sphere member 3 is adjustable so as to change the current value. The conductive sphere member 3 includes a first pressure sensor 31 electrically connected with the processor 16 and configured to detect the pressure forced on the conductive sphere member 3 so as to acquire a first pressure detecting result. The processor 16 is configured to control the power processing unit 10B based on the first pressure detected result so as to change the current value of the electric physiotherapy energy. In another embodiment, when successively receiving two pressure detected results in a unit time, the processor 16 controls the body physiotherapy machine to stop, to change the current frequency or to shift a square wave and a sin wave. Preferably, the conductive sphere member 3 is configured to detect a pain source and to display the pain source to the display unit 4.

The body 1 outputs optimized electric physiotherapy energy by ways of:

A) detecting and feed backing the acupuncture points, wherein when disease symptoms occur to the user, impedances of the acupuncture points change, such that the user knows his/her health status and sets the power parameters. The conductive sphere member 3 has a detection unit 32 configured to detect the acupuncture points and to acquire the impedances of the acupuncture points. The display unit 4 is fixed outside the body 1 and is connected with the processor 16 via another signal wire or in another wireless manner.

The body 1 further includes the processor 16 arranged therein and electrically connected with an acupuncture database 17 and the display unit 4, wherein the acupuncture database 17 has acupuncture data with respect to the acupuncture points, wherein the acupuncture data includes actual impedance data and diagnostic data. The processor 16 is configured to compare detected impedance data with actual impedance data, when the detected impedance data does not match with the actual impedance data, the users has a potential disease or an actual disease, and the processor 16 controls the display unit 4 to display the diagnostic data so that the user understands his/her health.

The acupuncture database 17 further has optimized output data with respect to the electric physiotherapy energy of the diagnostic data. The processor 16 acquires the optimized output data according to the diagnostic data and controls the display unit 4 to display the optimized output data with respect to the electric physiotherapy energy.

After the user views the optimized output data, the power parameters are adjustable by manually operating the operation unit 2. Alternatively, the body 1 automatically detects the acupuncture points and adjusts the power parameters, wherein the processor 16 controls the power parameters of the electric physiotherapy energy according to the optimized output data of the power.

The body 1 outputs the optimized electric physiotherapy energy by ways of:

A) judging and feed backing the user's data, wherein the body 1 judges user's detected data and provides optimized physiotherapy data to the user, wherein the user's detected data has a height, a weight, an age, a body fat, and a gender so as to adjust the power parameters of the electric physiotherapy energy, wherein the user's data is inputted by using the operation unit 2, and the body 1 further includes a user database 18 and the processor 16 connected with the user database 18, wherein the user database 18 has parameter data with respect to the user data, and the processor 16 selects matching data from the parameter data of the user database 18 based on the user data and controls the display unit 4 to display the matching data so that the user adjusts the power parameters of the electric physiotherapy energy according to the matching data.

The processor 16 judges and adjusts the user data and the matching data of the parameter data of the user database 18 based on at least one of the height, the weight, the age, the body fat, and the gender of the user's detected data. Preferably, the processor 16 automatically controls the electric physiotherapy energy according to the parameter data of the user database 18.

Figure 4:
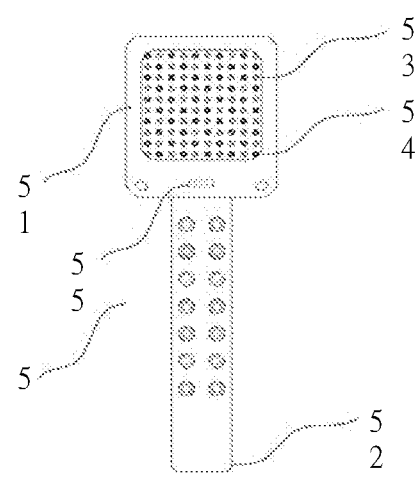
FIG. 4 is a schematic view showing the application of the physiotherapy machine according to the preferred embodiment of the present invention.

As shown in FIG. 4, the body physiotherapy machine treats the user physically by using:

1) a comb 5 electrically connected with the second output send 12, and the comb 5 includes a first segment 51, a second segment 52 configured to be held by the user, and multiple first brushers 53 made of conductive material, such that the comb 5 combs the user's head smoothly.

Preferably, the comb 5 is configured to heat the user's head to eliminate fatigue, wherein the comb 5 has a temperature monitor 55 configured to set a temperature value, and the comb 5 has multiple second brushers 54 arranged on a surface of the first segment 51, made of conductive materials respectively, and electrically connected with the temperature monitor 55 so that a temperature of the multiple second brushers 54 is maintained within the temperature value.

Figure 2:
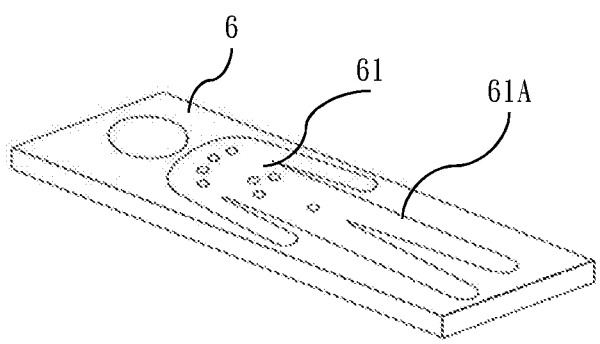
FIG. 2 is a schematic view showing the application of the physiotherapy machine according to the preferred embodiment of the present invention.

As illustrated in FIG. 2, the body physiotherapy machine treats the user physically by using:

2) a support member 6 which is any one of a seat cushion, a mattress, and a Yoga mat, wherein the support member 6 has a power transmission layer 61 configured to conduct the power and a third segment 12 accommodated in the support member 6 and connected with the power transmission layer 61.

The power transmission layer 61 is connected on a top or a bottom of the support member 6. Alternatively, as shown in FIG. 2, a part of the power transmission layer 61 is connected on the support member 6, wherein the power transmission layer 61 is defined by a first contour line 61A of a human figure. In another embodiment, the power transmission layer 61 is multiple power transmission bosses arranged on the support member 6.

The body 1 is accommodated in or is separated from the support member 6, wherein the third segment 13 is inserted into the support member 6 and is connected with the power transmission layer 61. When the support member 6 is the Yoga mat, the body 1 is separated from the support member 6. When the support member 6 is the seat cushion or the mattress, the body 1 is accommodated in the support member 6.

The support member 6 includes a second pressure sensor accommodated therein and electrically connected the body 1, when the user sits or lies on the support member 6, and the second pressure detects a pressure value is higher than a first preset value, the body 1 is controlled automatically to provide the electric physiotherapy energy to the user. When the user moves away from the support member 6, and the second pressure sensor detects the pressure value is lower than a second preset value, the body 1 is controlled automatically to stop and is set intelligently.

Referring to FIG. 2, the body 1 stimulates and eases the acupuncture points, such as of the user's body by using:

a) the mattress 6 on which the first contour line 61A is arranged and is configured to define the human figure, wherein the human figure has the power transmission layer 61 with respect to the acupuncture points, and the third output end 13 is electrically connected with a bottom of the power transmission layer 61, wherein the power transmission layer 61 is the multiple power transmission bosses so as to provide the electric physiotherapy energy to the user.

b) when the support member 6 is the seat cushion, the power transmission layer 61 is arranged on a top of the seat cushion 61 and is the multiple power transmission bosses with respect to the acupuncture points of user's buttocks respectively, wherein the third output end 13 is electrically connected with bottoms of the multiple power transmission bosses so as to simulate the acupuncture points of the user's buttocks.

c) When the support member 6 is the Yoga mat on which a second contour line is configured to define a human figure, wherein the human figure has the power transmission layer which is the multiple power transmission bosses with respect to the acupuncture points respectively, wherein the third output end 13 is electrically connected with bottoms of the multiple power transmission bosses so as to simulate the acupuncture points of the human figure, wherein the human figure is formed in any one of a palm shape, a foot shape, and a human shape. In another embodiment, the support member 6 is a foot mat.

The support member 6 further includes a first vibration unit accommodated therein and electrically connected with the body and the power transmission layer 61 so as to vibrate and massage the user and to simulate the cells of the user.

Figure 3:
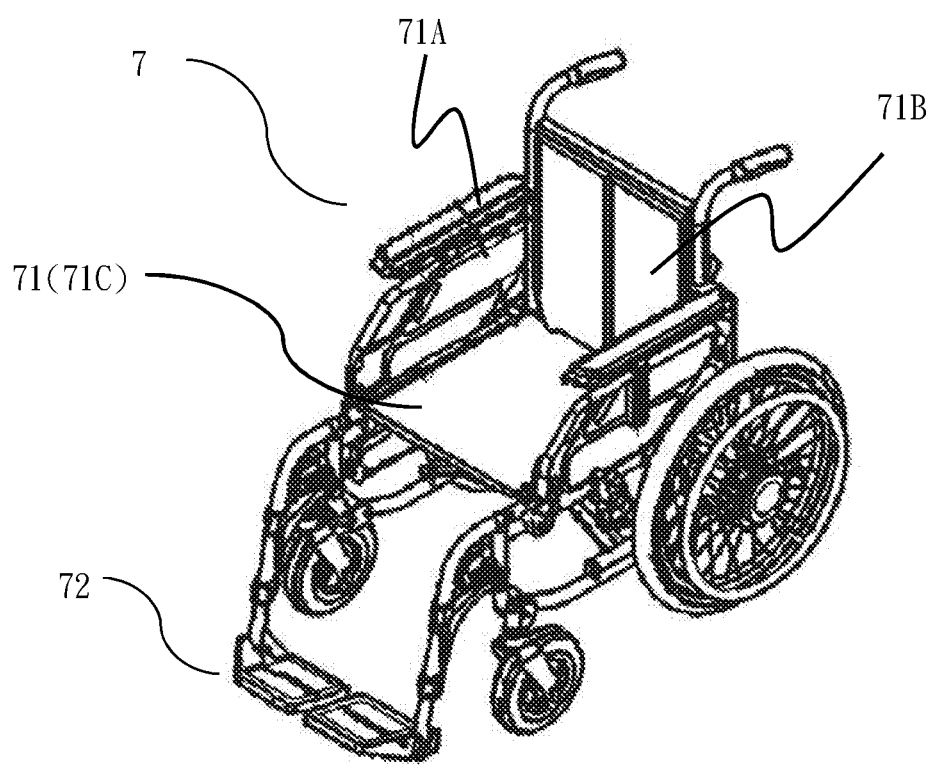
FIG. 3 is a schematic view showing the application of the physiotherapy machine according to the preferred embodiment of the present invention.

Preferably, the body 1 further includes apparel having the power transmission layer 61 the body 1 further includes a sixth output end 19 electrically connected the power processing unit and configured to output the electric physiotherapy energy, wherein the sixth output end 19 is also electrically connected with apparel so that the support member 6 provides the electric physiotherapy energy to the user via the cloth, wherein the apparel is any one of a cloth, a coat, a hat, a pant, a scarf, a vest, and a jacket.

d) When a medical auxiliary apparatus 7 contacts with the user, the body outputs the electric physiotherapy energy to the user. As shown in FIG. 3, the medical auxiliary apparatus 7 includes at least one contact face 71 configured to contact with the user, and the fourth output end 14 is connected with an inner surface of the contact face 71, such that the body 1 provides the electric physiotherapy energy to a hand, a back, and the buttocks of the user.

The medical auxiliary apparatus 7 is any one of an inversion table, a wheelchair, a walker, and a defecation chair. With reference to FIG. 3, the medical auxiliary apparatus 7 is the wheelchair and includes three contact faces 71A, 71B, 71C which contact with the hand, the back, and the buttocks of the user respectively. The body 1 is accommodated in or is separated from the medical auxiliary apparatus 7, wherein the fourth output end 14 is inserted into the medical auxiliary apparatus 7 to contact with the at least one contact face 71.

e) When the medical auxiliary apparatus 7 is the inversion table, the inversion table has a back fixing plate and a head fixing plate, wherein a first acupressure face is defined between the back fixing plate and the user and corresponds to the acupuncture points, and a second acupressure face is defined between the head fixing plate and the user and corresponds to the acupuncture points, wherein the fourth output end is electrically connected with the first acupressure face and the second acupressure face.

f) When the medical auxiliary apparatus 7 is the wheelchair, the wheelchair includes a seat cushion and a chair back, a third acupressure face is defined between the seat cushion and the user and corresponds to the acupuncture points, and a fourth acupressure face is defined between the chair back and the user and corresponds to the acupuncture points, wherein the fourth output end 14 is electrically connected with the third acupressure face and the fourth acupressure face, wherein the user's hands have the acupuncture points so that two armrests of the wheelchair are conductive to the user's hands, wherein the third acupressure face and the fourth acupressure face are electrically connected with the fourth output end.

g) When the medical auxiliary apparatus 7 is the walker, the walker includes a grip portion, and a fifth acupressure face is defined between the grip portion and the user and corresponds to the acupuncture points, wherein the fourth output end 14 is electrically connected with the fifth acupressure face.

In another embodiment, the medical auxiliary apparatus 7 includes a pedal 72 arranged on the wheelchair and corresponds to the acupuncture points of user's foot, wherein the pedal 72 has a foot portion defined by a foot contour line and corresponds to the acupuncture points of user's foot, and a sixth acupressure face is defined between the foot portion and the user and corresponds to the acupuncture points, wherein the fourth output end 14 is electrically connected with the sixth acupressure face. Preferably, the sixth acupressure face is conductive and is configured to provide the electric physiotherapy energy, thus simulating the acupuncture points effectively.

The conductive sphere member 3 includes a second vibration unit 33 configured to simulate the cells and to massage user's muscle and fascia. The fifth output end 15 of the body 1 is electrically connected with any one of a conductive sheet, a conductive clip, a conductive rod, and a conductive acupuncture needle. When the body 1 is applicable for the conductive acupuncture needle, the electric physiotherapy energy is sent to the acupuncture points via the conductive acupuncture needle. The conductive clip is clamped on a user's ear so that the body 1 sends the electric physiotherapy energy to the user. In another embodiment, the body 1 is electrically connected with a massage chair so that a chair back, a seat cushion, and two armrests of the massage provide the electric physiotherapy energy to the user.

The body 1 further incudes the fifth output end 15 electrically connected with a beauty product or the conductive sheet, wherein the beauty product is a beauty massager configured to activate and to massage user's skin by using the electric physiotherapy energy. When the beauty product is a face washing machine, the electric physiotherapy energy cleans user's face and skin. When the fifth output end 15 is connected with the conductive sheet attached on user's breast, the electric physiotherapy energy simulates the user's breast. Preferably, the body 1 mates with a breast pump to lift the user's breast.

While the preferred embodiments of the invention have been set forth for the purpose of disclosure, modifications of the disclosed embodiments of the invention and other embodiments thereof may occur to those skilled in the art. Accordingly, the appended claims are intended to cover all embodiments which do not depart from the spirit and scope of the invention.

What is claimed is:

1. A body physiotherapy machine comprising:
 a body including a power input end configured to electrically connected with a power supply unit, a power processing unit electrically connected with the power input end so as to adjust electric currents from the power supply unit to produce electric physiotherapy energy, a processor connected with the power processing unit, an operation unit electrically connected with the processor, a display unit connected with the processor so as to display physiotherapy energy information, and a first output ends configured to output the electric physiotherapy energy; and
 a conductive sphere member electrically connected with the first output end and configured to be held by a user so as to contact with the user directly or indirectly, thus sending the electric physiotherapy energy to the user,
 wherein the conductive sphere member includes a first pressure sensor electrically connected with the processor and configured to detect the pressure forced on the conductive sphere member so as to acquire a first pressure detecting result the processor is configured to control the power processing unit based on the first pressure detected result so as to change the current value of the electric physiotherapy energy,
 wherein the operation unit is configured to set power parameters of the electric physiotherapy energy, wherein the power parameters include a current value, a voltage value, the current frequency, and an operating time,
 wherein the conductive sphere member has a detection unit configured to detect acupuncture points of the user and to acquire impedances of the acupuncture points; the processor is electrically connected with an acupuncture database and the display unit, wherein the acupuncture database has acupuncture data with respect to the acupuncture points, wherein the acupuncture data includes actual impedance data and diagnostic data; the processor is configured to compare detected impedance data with the actual impedance data, when the detected impedance data does not match with the actual impedance data, and the processor controls the display unit to display the diagnostic data, wherein the acupuncture database further has optimized output data with respect to the electric physiotherapy energy of the diagnostic data; the processor acquires the optimized output data according to the diagnostic data and controls the display unit to display the optimized output data with respect to the electric physiotherapy energy, wherein the processor controls the power parameters of the electric physiotherapy energy according to the optimized output data of a power, wherein user's data is inputted by using the operation unit, and the body further includes a user database and the processor connected with the user database, wherein the user database has the parameter data with respect to user data, and the processor selects matching data from the parameter data of the user database based on the user data and controls the display unit to display the matching data, wherein the processor controls electric physiotherapy energy based on the matching data of the parameter data of the user database, and wherein the body further includes a second output end electrically connected with the power processing unit a comb electrically connected with the second output send, wherein the comb includes a first segment, a second segment configured to be held by the user, and multiple first brushers made of conductive material.

2. The body physiotherapy machine as claimed in claim 1, wherein the comb has a temperature monitor configured to set a temperature value, and the comb has multiple second brushers arranged on a surface of the first segment, made of conductive materials respectively, and electrically connected with the temperature monitor so that a temperature of the multiple second brushers is maintained within the temperature value.

3. The body physiotherapy machine as claimed in claim 2 further comprising a support member, wherein the support member has a power transmission layer configured to conduct the power and a third segment accommodated in the support member and connected with the power transmission layer.

4. The body physiotherapy machine as claimed in claim 3, wherein the support member includes a second pressure sensor accommodated therein and electrically connected the body, when the second pressure detects a pressure value is higher than a first preset value, the body is controlled automatically to operate; when the second pressure sensor detects the pressure value is lower than a second preset value, the body is controlled automatically to stop.

5. The body physiotherapy machine as claimed in claim 3 further comprising apparel having the power transmission layer; the body further includes a sixth output end electrically connected the power processing unit and configured to output the electric physiotherapy energy, wherein the sixth output end is also electrically connected with apparel.

6. The body physiotherapy machine as claimed in claim 5, wherein the support member is the mattress on which the first contour line is arranged and is configured to define a human figure, wherein the human figure has the power transmission layer with respect to the acupuncture points, and a third output end is electrically connected with a bottom of the power transmission layer, wherein the power transmission layer is multiple power transmission bosses.

7. The body physiotherapy machine as claimed in claim 2 further comprising a medical auxiliary apparatus which includes at least one contact face configured to contact with the user, wherein a fourth output end of the body is connected with an inner surface of the contact face.

8. The body physiotherapy machine as claimed in claim 7, wherein the medical auxiliary apparatus includes a pedal with respect to the acupuncture points of user's foot, wherein the pedal has a foot portion defined by a foot contour line and corresponding to the acupuncture points of the user's foot; and an acupressure face is defined between the foot portion and the user and corresponds to the acupuncture points, wherein the fourth output end is electrically connected with the acupressure face.

9. The body physiotherapy machine as claimed in claim 8, wherein the medical auxiliary apparatus is a wheelchair, the wheelchair includes a seat cushion and a chair back, a acupressure face is defined between the seat cushion and the user and corresponds to the acupuncture points, and another acupressure face is defined between the chair back and the user and corresponds to the acupuncture points, wherein the fourth output end is electrically connected with the acupressure face and another fourth acupressure face.

10. The body physiotherapy machine as claimed in claim 1, wherein the body includes a fifth output end electrically connected with any one of a conductive sheet, a conductive clip, a conductive rod, a conductive acupuncture needle, and a beauty product.

11. The body physiotherapy machine as claimed in claim 1, wherein the current frequency of the power parameters is more than $10^6$ Hz.

12. The body physiotherapy machine as claimed in claim 1, wherein the conductive sphere member includes a vibration unit.

* * * * *